United States Patent [19]

Sanden

[11] 4,228,192

[45] Oct. 14, 1980

[54] METHOD AND APPARATUS FOR THE QUANTITATIVE DETERMINATION OF BEER INGREDIENTS

[75] Inventor: Ulrich C. Sanden, Hildesheim, Fed. Rep. of Germany

[73] Assignee: Diessel GmbH & Co., Hildesheim-Bavenstedt, Fed. Rep. of Germany

[21] Appl. No.: 17,569

[22] Filed: Mar. 5, 1979

[30] Foreign Application Priority Data

Mar. 8, 1978 [DE] Fed. Rep. of Germany ....... 2809910

[51] Int. Cl.$^2$ .............................................. G01N 21/26
[52] U.S. Cl. .................................... 426/231; 250/339; 250/340
[58] Field of Search ................. 426/231; 250/339, 340

[56] References Cited

U.S. PATENT DOCUMENTS

| | | | |
|---|---|---|---|
| 3,161,768 | 12/1964 | Goulden | 250/339 |
| 3,212,854 | 10/1965 | Betts et al. | 426/231 X |
| 3,539,804 | 11/1970 | Billetdeaux et al. | 250/339 |

OTHER PUBLICATIONS

"Infrared Absorption Spectra" by R. T. O'Connor, Journal of American Oil Chemist Society, Nov. 55, vol. XXXII, No. 11, pp. 628–633.

Primary Examiner—Arthur D. Kellogg
Attorney, Agent, or Firm—Gilbert L. Wells

[57] ABSTRACT

The ingredients of beer and/or wort, particularly alcohol, extract, wort and carbon dioxide are determined individually by passing infrared light through the beer where a wavelength between 2.9 and 3.1 microns is used for the alcohol ingredient, a wavelength between 9.6 and 9.8 microns is used for the extract or the flavorings, and a wavelength from 4.2 to 4.4 microns is used for the carbon dioxide ingredient, each absorption of infrared being measured and analyzed.

8 Claims, 4 Drawing Figures

METHOD AND APPARATUS FOR THE QUANTITATIVE DETERMINATION OF BEER INGREDIENTS

CROSS-REFERENCE TO A RELATED APPLICATION

Applicant claims priority under 35 USC 119 for application No. P 28 09 910.7, filed Mar. 8, 1978 in the Patent Office of the Federal Republic of Germany

BACKGROUND OF THE INVENTION

The present invention relates to an apparatus and method for the quantitative analysis of the ingredients of beer and/or wort, the individual ingredients, namely alcohol, extract or wort and dissolved carbon dioxide being determined individually.

The state of the art of beer manufacturing may be ascertained by reference to the Kirk-Othmer, "Encyclopedia of Chemical Technology," Second Edition, vol. 3 (1964), pp. 297-338 under the section Beer and Brewing, particularly pp. 314-320 where fermentation is disclosed, the disclosure of which is incorporated herein.

In one known method of analysis of beer ingredients, the alcohol and extract determination is obtained using a refractometer. This is done by determining the various indices of refraction and by recording the density measurements. These two values provide the percentages of the ingredients. To determine the carbon dioxide content, the beer is placed in a vacuum and the carbon dioxide is measured on the basis of the degassing which takes place.

This prior art method suffers from the drawback that it is quite complex and in general it can be carried out only in the laboratory or under similar conditions. Furthermore, this prior art method is quite inaccurate because the boundary conditions such as fluctuations in pressure and temperature enter into the measured values and affect them. Lastly this known method suffers also from the drawback that it allows no in-line measurements.

SUMMARY OF THE INVENTION

Having in mind the limitations of the prior art, it is an object of the present invention to quantitatively analyze the ingredients of beer in the manufacture thereof while avoiding the prior art limitations in a very simple procedure which results in very accurate results.

This object is achieved by the present invention by transmitting infrared light through the beer and by using a wavelength between 2.9 and 3.1 microns to test the alcohol ingrredient, a wavelength between 9.6 and 9.8 microns to test the extract or the wort, and a wavelength between 4.2 and 4.4 microns to test the carbon dioxide ingredient. The particular infrared absorption is measured in each case and analyzed.

The present method achieves very accurate determination of the percentages of the particular ingredients when the wavelength ranges of the present invention are observed because these percentages and their absorptions are expressed by well defined magnitudes within the above cited ranges of wavelengths. Furthermore, the absorptivity in the infrared light is wholly independent of external conditions, i.e., independent of the pressures that prevail at the particular times and is extensively independent of the temperatures that exist. The process of the present invention furthermore is a method which can be implemented with instruments of low sensitivity and which therefore is applicable on a wide scale.

Therefore, the method of the present invention allows ascertining the individual ingredients of the beer and/or of the wort practically at any production station in the course of beer production without affecting the production procedure. Unlike the prior art method, that of the present invention does not require complex sampling under laboratory conditions, rather direct displays of the test values are feasible at the required stations. Neither special monitoring of the instrumentation nor trained professional help is requred.

As regards one embodiment for implementing the method of the present invention, it is especially advantageous to insert an attenuated-total-reflection (ATR) cell in the particular line through which the beer is passing. The liquid flowing around this cell allows in-line measurement of this liquid in the presence of multiple reflection. The initially cited wavelengths remain unaffected.

The instrumentation of the invention can operate with the known means of infrared spectroscopy wherein comparison measurements between the liquid to be tested on the one hand and water on the other are carried out to eliminate the pronounced water-absorptions which take place over wide ranges of the infrared. The liquid to be tested and the water are contained in two cells, and the known method switches with high frequency from one cell to the other to analyze the differences. In this manner the absorptivity of water is practically eliminated. Two cells with corresponding plumbing are required. When using an ATR in-line cell, an additional line of the same cross-section is needed for the water comparison medium, which must be supplied in addition.

Therefore, it is especially advantageous to make use of components of another known instrumentation in the apparatus of the present invention, this instrumentation relating to infrared spectroscopy in which switching takes place between two filters adjusted for the required wavelengths. Accordingly, the two filters are alternatingly placed into the beam, the switching frequency being about 100 Hz. One of the filter parameters (band-pass) corresponds to the above cited range of wavelengths permitting ascertainment of the percentage of the ingredient and the second filter parameter corresponds to a wavelength of from 1 to 2 microns above or below the above cited range of wavelengths for the individual ingredients. The difference between a maximum predetermined by the value of the ingredient and an adjacent base is thus formed.

The ATR cell, which ordinarily consists of sapphire, can be inserted transversely into the through-line depending on the latter's cross-section, the center plane of the cell coinciding with the cross-sectional diameter of the line. If only ATR cells of a specific size are available, or in order to keep the ATR cells small when the line diameters are large, it is especially advantageous to install the ATR cells offset from the center axis of the line, so that these cells form a secant to the cross-section of the line. In this manner even relatively small and short ATR cells can be mounted in very large lines while the accuracy of measurement is completely retained. Such an arrangement furthermore offers the advantage of practically leaving the line flow cross-section unaffected.

BRIEF DESCRIPTION OF THE DRAWING

The present invention is discussed further with reference to illustrative embodiments of the drawing, wherein.

DESCRIPTION OF THE PREFERRED EMBODIMENTS

Figure 1:
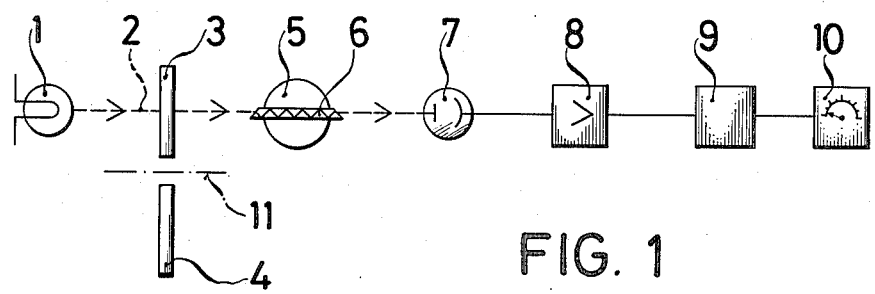
FIG. 1 is a schematic of an embodiment of the apparatus implementing the method of the present invention.

With particular reference to FIG. 1, an infrared source of light 1 is shown of which the beam 2 passes through filters 3 and 4 and through an ATR cell 6 inserted in line 5 to be incident on photocell 7. The output signals from photocell 7 vary depending on absorptivity and pass through an amplifier 8 to an analyzing stage 9 with a display 10.

Filters 3 and 4 are alternatingly brought at a relatively high frequency into beam 2, to which end they may be appropriately mounted in rotating manner about an axis 11. One of the filters corresponds to the range of wavelengths of the beam used for testing, while the other filter deviates by 1 to 2 microns above or below from the given range. In this manner, the difference between the test values for the individual ingredients in the range of wavelengths provided by the present invention on the one hand and an adjacent comparison base is formed, so that the recorded maxima permitting the determination of the percentages tested for are easily detected.

Figure 2:
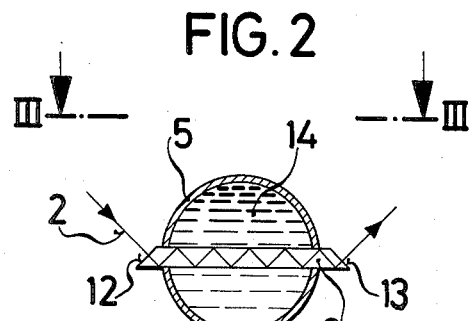
FIG. 2 is a schematic of a line cross-section with inserter ATR cell.

FIG. 2 is a schematic of the arrangement of the ATR cell 6 of FIG. 1 when coincident with the cross-sectional diameter of line 5. ATR cell 6 is so installed in the line that its entry and exit surfaces 12 and 13 are outside the line. As indicated, the liquid 14 flows around the surfaces of the ATR cell.

Beyond filters 3 and 4, the beam 2 enters the ATR cell in the region of surface 12, and is multiply reflected inside this cell (ordinarily 25 times), then exits through surface 13. Very accurate in-line measurement is made possible in this manner.

Figure 3:
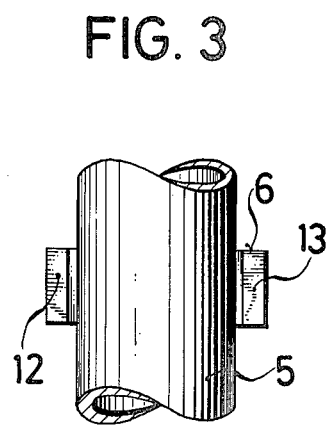
FIG. 3 is the view III—III of FIG. 2.

FIG. 3 is the view III—III of FIG. 2 and indicates the entry and exit surfaces 12 and 13 of ATR cell 6, which project from the line.

Figure 4:
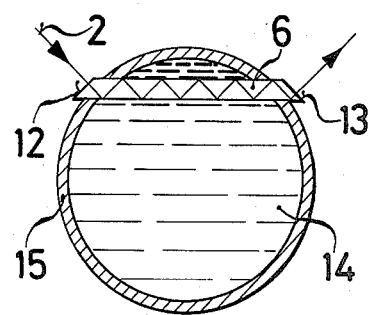
FIG. 4 is a view similar to FIG. 2 for a through-line of relatively large cross-section.

FIG. 4 is similar to FIG. 2, but for another embodiment. In this case the ATR cell 6 is inserted into a line 15 of fairly large cross-section and in such manner that it forms a chord with the cross-section circle of the line. In this arrangement too, the entry and exit surfaces 12 and 13 of the ATR cell are outside, and liquid 14 flows on both sides of the ATR cell. In spite of the relatively large cross-section of line 15, a relatively small and short ATR cell can nevertheless be used while retaining full accuracy of measurement. Further, the flow cross-section of line 15 is less affected for such an arrangement than if the ATR cell were mounted in coincidence with the cross-sectional diameter of the line.

Three pairs of filter are needed for the three ranges of wavelength of the present invention, these pairs being mounted in interchangeable manner, or else filters are used which can vary continuously within the above indicated ranges.

Especially good measurements are achieved by using a wavelength of 3.0 microns for the alcohol ingredient and a wavelength of 4.27 microns for the carbon-dioxide ingredient.

I claim:

1. A method for quantitatively determining the alcohol, wort, and carbon dioxide ingredients of beer comprising:
   (a) passing said beer through a conduit;
   (b) passing infrared light having a first wavelength between 2.9 and 3.1 microns through said beer in said conduit;
   (c) passing infrared light having a second wavelength between 9.6 and 9.8 microns through said beer in said conduit;
   (d) passing infrared light having a third wavelength between 4.2 and 4.4 microns through said beer in said conduit;
   (e) measuring the absorption of said first wavelength and displaying an alcohol percentage;
   (f) measuring the absorption of said second wavelength and displaying a wort percentage; and
   (g) measuring the absorption of said third wavelength and displaying a carbon dioxide percentage.

2. An apparatus for quantitatively determining the alcohol, wort and carbon dioxide ingredients of beer, comprising:
   (a) a first infrared source generating a beam having a wavelength between 2.9 and 3.1 microns along a first optical axis;
   (b) a second infrared source generating a beam having a wavelength between 9.6 and 9.8 microns along a second optical axis;
   (c) a third infrared source generating a beam havng a wavelength between 4.2 and 4.4 microns along a third optical axis;
   (d) a line passing said beer having a flow axis;
   (e) a first attenuated total reflection cell located along said first optical axis and through said flow axis;
   (f) a second attenuated total reflection cell located along said second optical axis and through said flow axis;
   (g) a third attenuated total refelection cell located along said third optical axis and through said flow axis;
   (h) means for measuring and displaying the absorptivity of said first infrared source to give said alcohol percentage;
   (i) means for measuring and displaying the absorptivity of said second infrared source to give said wort percentage; and
   (j) means for measuring and displaying the absorptivity of said third infrared source to give said carbon dioxide percentage.

3. The apparatus of claim 2, further comprising a second line for water and a second attenuated total reflection cell for comparison measurements with water.

4. The apparatus of claim 2 further comprising first and second filters (3,4) along said optical axis in said beam (2) in front of said reflection cell and means for alternatingly moving said filters into position into said beam, said first filter corresponding to the range of wavelength of a measuring beam and said second filter deviating by 1 to 2 microns from said first.

5. The apparatus of claim 4, wherein means for alternatingly moving said filters (3,4) are actuated at a frequency of about 100 Hz.

6. The apparatus of claim 2, wherein said reflection cell (6) is mounted transversely through said line (5), its center plane coinciding with the cross-sectional diameter of said line (5).

7. The apparatus of claim 2, wherein said reflection cell (6) is mounted offset from said flow axis of said line (15) and forms a secant with respect to the cross-section of said line (15).

8. The method of claim 1, wherein the wavelength for the alcohol ingredient is 3.0 microns and the wavelength for the carbon dioxide ingredient is 4.27 microns.

* * * * *